(12) United States Patent
Bonrath et al.

(10) Patent No.: US 9,370,772 B2
(45) Date of Patent: Jun. 21, 2016

(54) CATALYTIC SYSTEM

(71) Applicant: DSM IP ASSETS B.V., Heerlen (NL)

(72) Inventors: Werner Bonrath, Basel (CH); Axel Buss, Basel (CH); Jonathan Alan Medlock, Basel (CH); Thomas Mueller, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/408,088

(22) PCT Filed: Jun. 21, 2013

(86) PCT No.: PCT/EP2013/062956
§ 371 (c)(1),
(2) Date: Dec. 15, 2014

(87) PCT Pub. No.: WO2013/190076
PCT Pub. Date: Dec. 27, 2013

(65) Prior Publication Data
US 2015/0165431 A1    Jun. 18, 2015

(30) Foreign Application Priority Data

Jun. 22, 2012 (EP) .................................... 12173191

(51) Int. Cl.
| | | |
|---|---|---|
| *C07C 45/62* | (2006.01) |
| *B01J 31/00* | (2006.01) |
| *B01J 37/00* | (2006.01) |
| *B01J 35/02* | (2006.01) |
| *B01J 23/62* | (2006.01) |
| *B01J 37/02* | (2006.01) |
| *B01J 27/232* | (2006.01) |
| *B01J 37/06* | (2006.01) |

(52) U.S. Cl.
CPC .............. *B01J 35/026* (2013.01); *B01J 23/628* (2013.01); *B01J 27/232* (2013.01); *B01J 35/023* (2013.01); *B01J 37/024* (2013.01); *C07C 45/62* (2013.01); *B01J 37/06* (2013.01); *C07C 2101/16* (2013.01)

(58) Field of Classification Search
CPC ............ B01J 23/62; B01J 31/00; C07C 45/62
USPC .................................. 502/339, 439; 568/350
See application file for complete search history.

(56) References Cited

U.S. PATENT DOCUMENTS 2,780,658 A * 2/1957 Surmatis ........................ 570/217
2012/0053353 A1   3/2012 Bonrath et al.

OTHER PUBLICATIONS

International Search Report for PCT/EP2013/062956, mailed Aug. 29, 2013, 2 pages.

* cited by examiner

*Primary Examiner* — Sikarl Witherspoon
(74) *Attorney, Agent, or Firm* — Nixon & Vanderhye P.C.

(57) ABSTRACT

The present invention relates to a new catalytic system, which is a Lindlar type catalyst, wherein the supporting material ($CaCO_3$) has an average particle size (d50) of more than 10 Pm, as well as to the use of such a catalytic system for the partial hydrogenation of a carbon-carbon triple bond (to a carbon-carbon double bond).

3 Claims, No Drawings

CATALYTIC SYSTEM

This application is the U.S. national phase of International Application No. PCT/EP2013/062956, filed 21 Jun. 2013, which designated the U.S. and claims priority to EP Application No. 12173191.3, filed 22 Jun. 2012, the entire contents of each of which are hereby incorporated by reference.

The present invention relates to a new catalytic system, which is a Lindlar type catalyst, wherein the supporting material ($CaCO_3$) has an average particle size (d50) of more than 10 μm, as well as to the use of such a catalytic system for the partial hydrogenation of a carbon-carbon triple bond (to a carbon-carbon double bond).

Lindlar catalysts are very important and well known catalysts. A Lindlar catalyst is a heterogeneous catalyst that consists of palladium deposited on calcium carbonate and treated with various forms of lead. The catalyst is used for the hydrogenation of alkynes to alkenes (i.e. without further reduction into alkanes). Thus if a compound contains a double bond as well as a triple bond, only the triple bond is reduced to a double bond.

Due to the importance of this type of catalyst it is always of interest to improve this catalyst. The aim of the present work was to improve the selectivity of the hydrogenation reaction catalyzed by the Lindlar type catalyst.

Surprisingly, it was found that when the supporting material, which is $CaCO_3$, has an average particle size (d50) of more than 10 μm the selectivity of the hydrogenation process is significantly increased.

Therefore the present invention relates to a Lindlar type catalyst, wherein the supporting material ($CaCO_3$) has an average particle size of more than 10 μm.

A Lindlar type catalyst is a heterogeneous catalyst that consists of palladium deposited on calcium carbonate and treated with various forms of lead.

The particle size as well as the particle size distribution can be determined by using a commonly known method, such as sieve analysis, photoanalysis, optical counting methods, electroresistance counting methods, sedimentation techniques, laser diffraction methods or acoustic spectroscopy or ultrasound attenuation spectroscopy).

For the determination of the particle size and distribution, the laser diffraction method was used. Measurements were obtained using a HELOS/KF laser diffraction apparatus (from Sympatec GmbH, D-38678 Clausthal-Zellerfeld, Germany). Calcium carbonate samples were shaken to remove agglomerates, suspended in water in a 50 ml cuvette and then analyzed by using a He—Ne laser at 632.8 nm.

The minimum size of the $CaCO_3$ particles (d50) of the catalyst according to the present invention is more than 10 μm.

d50 is the mass-median-diameter (MMD). 50% of all particles have a size of 10 μm or more. The MMD is considered to be the average particle diameter by mass.

The particles are usually not larger than 120 μm.

The Lindlar type catalyst (I) has the following composition
(i) 85 weight-% (wt-%)-99.85 wt-%, based on the total weight of the catalyst, of $CaCO_3$, and
(ii) 0.1 wt-%-10 wt-%, based on the total weight of the catalyst, of Pd, and
(iii) 0.05 wt-%-5 wt-%, based on the total weight of the catalyst, of Pb,
characterized in that the average particle size (d50) of the $CaCO_3$ particles is between 10 μm and 120 μm.

Preferably the Lindlar type catalyst (II) has the following composition
(i) 89 wt-%-96 wt-%, based on the total weight of the catalyst, of $CaCO_3$, and
(ii) 3 wt-%-7 wt-%, based on the total weight of the catalyst, of Pd, and
(i) 1 wt-%-4 wt-%, based on the total weight of the catalyst, of Pb,
characterized in that the average particle size (d50) of the $CaCO_3$ particles is between 10 μm and 120 μm.

The sum of all % adds always up to 100.

A very preferred embodiment is Lindlar type catalyst (III) comprising
(i) 92.5 wt-%, based on the total weight of the catalyst, of $CaCO_3$
(ii) 5 wt-%, based on the total weight of the catalyst, of Pd
(iii) 2.5 wt-%, based on the total weight of the catalyst, of Pb,
characterized in that the average particle size (d50) of the $CaCO_3$ particles is between 10 μm and 120 μm.

The Lindlar type catalyst according to the present invention is prepared according to commonly known method. It is essential that the average particle size of the $CaCO_3$ particles is more than 10 μm (d50) and not larger than 120 μm, preferably not larger than 100 μm.

Therefore more preferred catalysts (IV) according to the present invention are catalysts (I), (II) and/or (III), characterized in that the average particle size (d50) of the $CaCO_3$ particles is between 10 μm and 100 μm.

The average particle size of the $CaCO_3$ particles is the essential feature of the catalyst of the present invention. The average particle size can be achieved and controlled by processes well known from the prior art.

This is achieved for example by precipitation processes. The preparation of calcium carbonates with defined particle sizes has been described in EP 1 607 373 and EP 0 406 662.

$CaCO_3$ particles with average particle sizes (d50) of 10 μm-120 μm (or 10 μm-100 μm) are also available commercially. For example from Specialty Minerals Inc (Bethlehem, USA).

The catalyst according to the present invention can be produced in a two step process:

In a first step the $CaCO_3$ particles (with the well defined particle sizes) are produced. These so produced $CaCO_3$ particles are then used in the production of the Lindlar type catalysts.

A very suitable way of the production of the catalysts according to the present invention is disclosed in Example 1.

The catalysts according to the present invention are used for the partial hydrogenation of carbon-carbon triple bonds.

This type of catalyst is for example very suitable for the partial hydrogenation of 6-hydroxy-3-(5-hydroxy-3-methyl-pent-3-in-1-ynyl)-2,4,4-trimethylcyclohex-2-enone (KPL) to 6-hydroxy-3-(5-hydroxy-3-methyl-penta-1,3-dienyl)-2,4,4-trimethylcyclohex-2-enone (KDL).

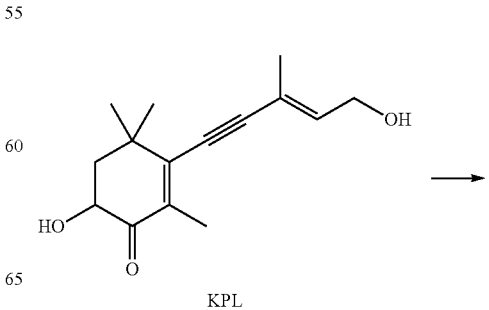

KPL

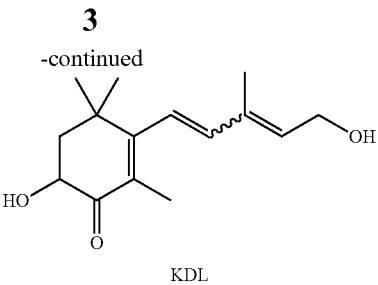

KDL

The following examples serve to illustrate the invention. The temperature is given in ° C. and all percentages are related to the weight.

EXAMPLES

Example 1

Preparation of Palladium-Lead Lindlar Catalysts

A palladium stock solution was prepared by the addition of 40.3 g of deionised water to 40.1 g of a dihydrogen tetrachloropalladate (II) solution (10% Pd). 1N Sodium Hydroxide solution was added to adjust the pH to 4.0

In a 100 ml glass reactor, 9.0 g of precipitated calcium carbonate (from Specialty Minerals Inc.) was suspended in 50 ml of deionised water with stirring. To the reaction mixture was added 17.25 g of palladium stock solution over 20 minutes. After the addition, the mixture was stirred at room temperature for 10 minutes and then heated until an internal temperature of 85° C. was reached. 4.95 ml of 0.7 M sodium formate solution was added over 10 minutes and the reaction mixture was stirred for an additional 40 minutes. The hot solution was filtered and sucked dry.

The palladium on calcium carbonate catalyst was re-suspended in 100 ml deionised water and stirred for at least 5 minutes. The suspension was filtered and the catalyst was sucked dry. This washing procedure was repeated until all soluble inorganic salts had been washed out of the catalyst. The powder obtained was dried overnight in a vacuum oven (65° C., 10-30 mbar).

5.0 g of the dried powder was suspended in 30 ml of deionised water and was stirred for 10 minutes. 2.4 ml of a 7.7 wt-% Pb(OAc)$_2$ solution was added over 10 minutes and the mixture was stirred for an additional 10 minutes. The mixture was heated to an internal temperature of 80° C. for 45 minutes and then allowed to cool. After filtration, the catalyst was washed twice by suspension in 100 ml deionised water followed by filtration, as described above. The catalyst was dried at 55° C. in a vacuum oven (10-30 mbar) overnight to yield the desired palladium-lead catalyst (4.80-5.10 g).

Example 2

Hydrogenation of KPL 250 mg of KPL was added to a 8 ml glass reactor and 1.8 g of 1:1 ethanol:water was added. Catalyst of Example 1 (10-100 mg) and catalyst poison (20 mg of a 0.13 wt-% solution in water of Tegochrome 22) were added and the reactor was sealed. The reactor was purged with argon 5 times (by pressurising to 5 bar followed by release of the pressure) and 3 times with hydrogen (pressurise to 3 bar then release). The reaction mixture was heated to 28° C., pressurised to 3 bar hydrogen and stirred at 600 rpm until consumption of 100% of the theoretical consumption was observed.

All the following catalysts and the hydrogenations have been made in analogy to Example 1 and 2. Only the size of CaCO$_3$ and the concentration of the catalyst have been varied.

In Table 1 there are the examples which are falling under the scope of the present invention. In Table 2, these examples serve as comparison example. All these catalyst do have smaller CaCO$_3$ particle sizes.

TABLE 1

Inventive Examples

| Example | d50 [μm] | Amount Cat [mg] | Selectivity [%] | Conversion [%] |
|---|---|---|---|---|
| 3 | 63.91 | 46 | 99.04 | 81.53 |
| 4 | 14.62 | 46 | 92.12 | 77.02 |
| 5 | 13.84 | 46 | 90.29 | 76.93 |

TABLE 2

Comparative Examples

| Example | d50 [μm] | Amount Cat [mg] | Selectivity [%] | Conversion [%] |
|---|---|---|---|---|
| 6 | 8.74 | 51 | 70.84 | 67.57 |
| 7 | 1.59 | 46 | 69.2 | 66.54 |
| 8 | 4.33 | 21 | 71.84 | 66.14 |
| 9 | 6.37 | 52 | 74.89 | 69.27 |
| 10 | 4.20 | 101 | 55.12 | 63.28 |
| 11 | 3.25 | 58 | 61.93 | 62.60 |

It can be seen that hydrogenations, wherein the average particle size of the CaCO$_3$ particles are smaller than 10 μm, do not achieve the same selectivity.

The invention claimed is:

1. A method for the partial hydrogenation of 6-hydroxy-3-(5-hydroxy-3-methyl-pent-3-in-1-ynyl)-2,4,4-trimethylcyclohex-2-enone to 6-hydroxy-3-(5-hydroxy-3-methyl-penta-1,3-dienyl)-2,4,4-trimethylcyclohex-2-enone, the method comprising:
   (a) subjecting 6-hydroxy-3-(5-hydroxy-3-methyl-pent-3-in-1-ynyl)-2,4,4-trimethylcyclohex-2-enone to conditions of at least partial hydrogenation in the presence of a Lindlar-type catalyst which comprises, based on total weight of the catalyst:
      (i) 85 wt. % to 99.85 wt. % of CaCO$_3$ having an average particle size (d50) of 10 μm to 120 μm,
      (ii) 0.1 wt. % to 10 wt. % of Pd, and
      (iii) 0.05 wt. % to 5 wt. % of Pb; and
   (b) obtaining 6-hydroxy-3-(5-hydroxy-3-methyl-penta-1,3-dienyl)-2,4,4-trimethylcyclohex-2-enone from the partial hydrogenation conditions of step (a) at a selectivity of greater 90%.

2. The method according to claim 1, wherein the catalyst comprises, based on total weight of the catalyst:
   (i) 89 wt. % to 96 wt. % of CaCO$_3$,
   (ii) 3 wt. % to 7 wt. % of Pd, and
   (iii) 1 wt. % to 4 wt. % of Pb.

3. The method according to claim 1, wherein the catalyst comprises, based on total weight of the catalyst:
   (i) 92.5 wt. % of CaCO$_3$,
   (ii) 5 wt. % of Pd,
   (iii) 2.5 wt. % of Pb.

* * * * *